United States Patent [19]

Shustorovich et al.

[11] Patent Number: 5,387,569
[45] Date of Patent: Feb. 7, 1995

[54] CATALYTIC SOLUTION SUITABLE FOR CONVERTING COMBUSTION EMISSIONS

[75] Inventors: Eugene Shustorovich, Pittsford, N.Y.; Richard Montano, Vienna, Va.; Aleksandr Bragin, Moscow; Veniamin Kalner, Moscow, U.S.S.R.; Konstantin Solntsev, Moscow, U.S.S.R.; Nikolai Moiseev, Moscow, U.S.S.R.; Yuri Buslaev, Moscow, U.S.S.R.

[73] Assignee: Blue Planet Technologies Co., L.P., New York, N.Y.

[21] Appl. No.: 841,356

[22] Filed: Feb. 25, 1992

[51] Int. Cl.6 .............................. B01J 31/28
[52] U.S. Cl. .................... 502/162; 502/166; 502/167; 502/169; 502/170; 502/172; 502/230; 502/300; 502/344
[58] Field of Search ................ 502/161, 162, 166, 167, 502/169, 170, 172, 230, 300, 344

[56] References Cited

U.S. PATENT DOCUMENTS

| | | |
|---|---|---|
| 1,989,113 | 1/1935 | Rector . |
| 2,086,775 | 7/1937 | Lyons et al. . |
| 2,151,432 | 3/1939 | Lyons et al. . |
| 2,194,186 | 3/1940 | Pier et al. . |
| 2,800,172 | 7/1957 | Romer et al. . |
| 3,348,932 | 10/1967 | Kukin . |
| 3,450,116 | 6/1969 | Knight et al. . |
| 3,537,434 | 11/1970 | Herpin . |
| 3,716,040 | 2/1973 | Herpin . |
| 3,746,498 | 7/1973 | Stengel . |
| 3,773,894 | 11/1973 | Bernstein et al. . |
| 3,800,532 | 4/1974 | Schischkow . |
| 3,856,901 | 12/1974 | Neumann et al. . |
| 3,862,819 | 1/1975 | Wentworth . |
| 3,875,922 | 4/1975 | Kirmss . |
| 3,929,118 | 12/1975 | Leong . |
| 3,953,369 | 4/1976 | Ohara et al. . |
| 4,016,837 | 4/1977 | Wentworth et al. . |
| 4,024,079 | 5/1977 | Okuyama et al. . |
| 4,048,098 | 9/1977 | Koberstein et al. . |
| 4,064,037 | 12/1977 | Graven et al. . |
| 4,064,039 | 12/1977 | Penick . |
| 4,085,145 | 4/1978 | Mimoun et al. ............. 260/592 |
| 4,090,838 | 5/1978 | Schena . |
| 4,118,339 | 10/1978 | Latos . |
| 4,170,960 | 10/1979 | Germack et al. . |
| 4,203,895 | 5/1980 | Parcell et al. ............. 549/399 |
| 4,214,615 | 7/1980 | Boyer . |
| 4,295,816 | 10/1981 | Robinson . |
| 4,317,918 | 3/1982 | Takano et al. ............. 568/807 |
| 4,362,130 | 12/1982 | Robinson . |
| 4,382,017 | 5/1983 | Robinson . |
| 4,410,467 | 10/1983 | Wentworth . |
| 4,419,967 | 12/1983 | Protacio et al. . |
| 4,475,483 | 10/1984 | Robinson . |
| 4,476,339 | 10/1984 | Reinhard et al. . |
| 4,542,226 | 4/1985 | Eddy et al. ............. 549/214 |
| 4,631,076 | 12/1986 | Kurihara . |
| 4,646,516 | 3/1987 | Bostock . |
| 4,665,690 | 5/1987 | Nomoto et al. . |
| 4,752,302 | 6/1988 | Bowers et al. . |
| 4,757,045 | 7/1988 | Turner et al. . |
| 4,842,617 | 6/1989 | Kukin . |
| 4,863,889 | 9/1989 | Passaretti-Miscia . |
| 4,891,050 | 1/1990 | Bowers et al. . |
| 4,892,562 | 1/1990 | Bowers et al. . |
| 5,094,821 | 3/1992 | Hitachi et al. . |

Primary Examiner—Asok Pal
Attorney, Agent, or Firm—Kenyon & Kenyon

[57] ABSTRACT

A catalyst solution comprising one or more compounds of a metal catalyst and an organic solvent selected from the group consisting of a glycol derivative, an alkyl pyrrolidone, and an alkoxy ethyl ether, wherein no additional chloride-containing compounds are added to the solution. The metal can be selected from the group consisting of platinum, rhenium and rhodium. The compounds can be selected from the group consisting of $H_2PtCl_6.6H_2O$, $Re_2(CO)_{10}$, $Re_2O_7$, $LiReO_4$ and $RhCl_3.4H_2O$. The catalytic solutions are useful in conversion of pollutants from automotive engines and the like. In a particularly preferred embodiment, the solution contains three metals: platinum, rhenium, and rhodium.

15 Claims, 1 Drawing Sheet

CATALYTIC SOLUTION SUITABLE FOR CONVERTING COMBUSTION EMISSIONS

FIELD OF THE INVENTION

This invention relates to catalytic solutions, more particularly to solutions containing metallic compounds useful in assisting conversion of materials such as those present in emissions from automotive engines.

BACKGROUND OF THE INVENTION

There has long been a need to employ catalysts in reactions such as simultaneous combustion of carbon monoxide, unburned hydrocarbons and the reduction of nitrogen oxides (NOx) which are emitted from automotive engines and the like. The role of catalysts, particularly three-way catalysts, in automotive emission control has been widely studied in the art. For example, Taylor, "Automobile Catalytic Converter", *Catalysis, Science and Technology*, pp. 119–67 (Anderson et al. eds. 1984), describes emission control technology, composition of three-way catalysts, and catalytic supports.

Conventional systems for converting automotive exhaust gases employ a pre-fabricated supported catalyst, typically a solid stratum of catalyst material, such as honeycombed ceramic structures, which are placed in the exhaust section of the automobile. As the emissions pass through the solid, the catalytic metal present on the strata aids in conversion of CO, NOx and unburned hydrocarbons to $CO_2$, $N_2$ and $H_2O$. However, the solid strata-type catalytic converter eventually become spent, and require removal and replacement in the exhaust portion of the engine. Moreover, structures such as a honeycomb support are complex and relatively expensive to manufacture. State of the art systems capable of carrying out three-way catalysis include those having supported noble metals such as rhodium and platinum metals, with rhodium being a preferred catalyst for the reaction:

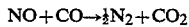

$$NO + CO \rightarrow \tfrac{1}{2} N_2 + CO_2$$

Platinum is the preferred catalyst for oxidation of CO and unburned hydrocarbons.

The noble metals are expensive and in limited supply, particularly rhodium. This situation is exacerbated by the fact that current usage of platinum and rhodium in three-way catalysis exceeds the mine ratio of Rh/Pt. Thus, reduction of noble metal usage is a problem in three-way catalysis. Therefore, it is necessary to develop alternative approaches to emission control.

Accordingly, there is a need for alternative methods of converting automotive emissions not utilizing conventional additional, pre-fabricated, non-regenerable solid catalytic material-containing supports in the exhaust system of an automobile.

U.S. Pat. Nos. 4,295,816, 4,382,017 and 4,475,483 describe catalyst solutions and delivery systems for improving the efficiency of combustion chambers. The catalyst solutions described in U.S. Pat. No. 4,382,017 comprise a single metal catalyst compound, $H_2PtCl_6.6H_2O$; a chloride compound such as HCl, LiCl, or NaCl; an antifreeze compound such as ethylene glycol; and approximately 50 percent water by volume. The chloride is a blocking agent which prevents precipitation and destruction of the platinum compound which is said would otherwise occur by use of the antifreeze compound. The solutions are not taught or suggested for use in aiding conversion of automotive emissions, require the chloride "blocking agent," and contain undesirably high levels of water.

U.S. Pat. No. 4,295,816 describes a catalyst delivery system including a single platinum group metal catalyst in water. A layer of oil containing a manganese catalyst is provided on top of the surface of the water. Air is bubbled through the water and is said to meter minute amounts of catalyst to a combustion system, where the catalyst is consumed in the combustion reaction. The patent does not teach or suggest use of a solvent such as a glycol derivative, or that the solution would contain desirable viscosity and other characteristics to permit entrainment of metal compounds upon passing air over the solution, or that the solution could be used for deposition onto a surface within the exhaust system of an automobile. The patent does not teach or suggest conversion of emissions from combustion chambers.

U.S. Pat. No. 4,475,483 describes a catalyst delivery system similar to that described in U.S. Pat. No. 4,295,816, with a single rhenium metal catalyst used in place of a platinum group metal catalyst in the water. The patent further describes that an antifreeze agent such as a glycol, dissolved the water along with the catalyst. The patent teaches that if an antifreeze agent is employed, a blocking agent such as NaCl, HCl, or LiCl must be employed to prevent precipitation of the catalyst. The patent does not teach or suggest conversion of emissions from a combustion chamber.

OBJECTS AND SUMMARY OF THE INVENTION

In light of the foregoing, it is an object of the invention to provide a catalytic material capable of converting emissions from automotive engines.

It is a further object of the invention to provide a catalytic containing-material capable of converting automotive emissions without the need for additional, non-regenerable catalytic solid support system in the exhaust portion of a engine. It is a further object of this invention to provide a catalytic material capable of converting automotive emissions via repetitive delivery of catalyst from a liquid source as needed.

These and other objects of the invention are accomplished by a catalytic solution comprising at least one metal catalyst compound, preferably three metal catalyst compounds, and an organic solvent selected from the group consisting of a glycol derivative, preferably a diethylene glycol derivative, an alkyl pyrrolidone and an alkoxy ethyl ether, wherein no additional chloride-containing compounds are added to the solution. The metal can be selected from the group consisting of platinum, rhenium and rhodium. The compounds can be selected from the group consisting of $H_2PtCl_6.6H_2O$, $Re_2(CO)_{10}$, $Re_2O_7$, $LiReO_4$ and $RhCl_3.4H_2O$. The solutions are useful in reduction of pollutants from automotive engines and the like.

DETAILED DESCRIPTION OF THE PREFERRED EMBODIMENTS

Figure 1:
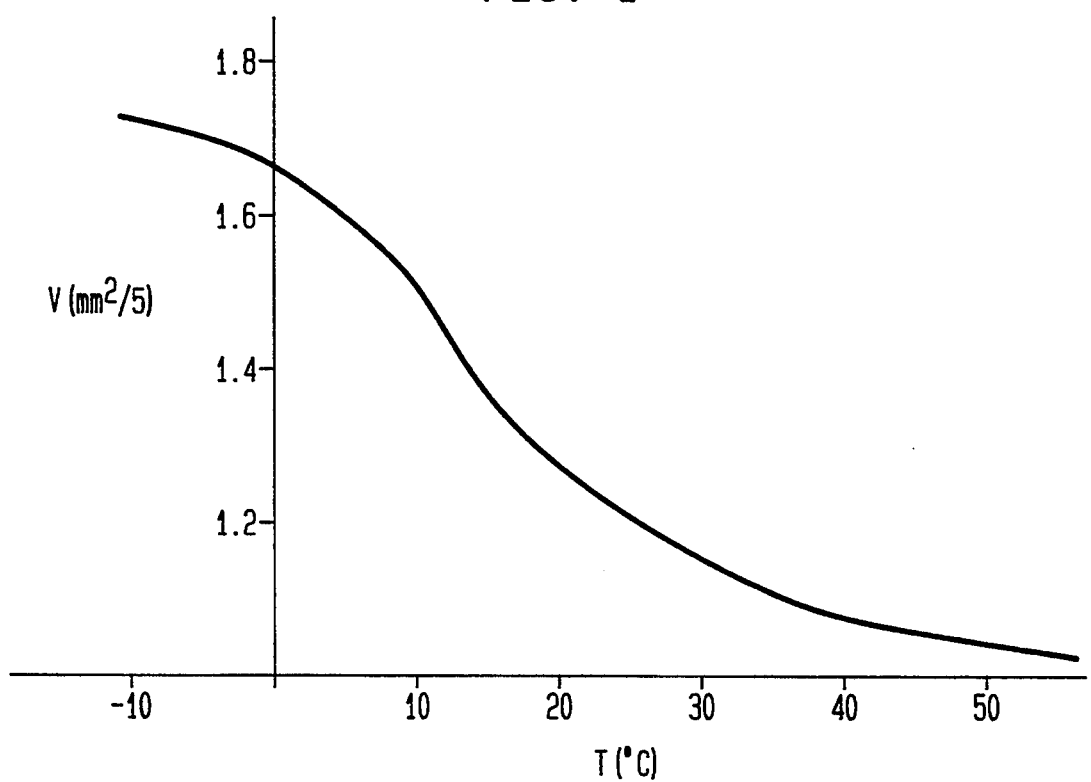
FIG. 1 is a graph of the viscosity of a solution of the present invention over a temperature range.

The catalytic solutions of the present invention contain one or more metal compounds in a suitable solvent. Metals useful in the present invention include middle transition metals such as Group VIIA metals, including rhenium, and ending transition metals such as Group VIIIA metals including platinum, and rhodium.

The metals are present in compound forms such as chlorides, carbonyls, perrhenates, and oxides in the solution. The compounds should be of a form which renders the metal soluble in the solvent, permits entrainment of the metal in an air stream such as the incoming air stream into an automotive engine, and permits deposition of the metal onto a surface such as the automotive exhaust system under desired temperature and pressure conditions. Selection of appropriate compounds should also provide that upon deposition of the metal on a tailpipe, muffler, or other suitable deposition surface in the exhaust system, an efficient dispersion of catalytic material is effected on the surface so that efficient conversion of CO, NOx and unburned hydrocarbons takes place as these compounds contact the deposited metal.

Where platinum is employed as a metal in the invention, the preferred compound form is $H_2PtCl_6.6H_2O$. For rhenium, suitable compounds are $Re_2(CO)_{10}$, $Re_2O_7$, or $LiReO_4$, with $LiReO_4$ and $Re_2(CO)_{10}$ preferred, and $LiReO_4$ particularly preferred. For rhodium, the preferred compound is $RhCl_3.4H_2O$.

Preferred solvents for the metal compounds include glycol derivatives, and in particular diethylene glycol derivatives such as diglyme $[CH_3O(CH_2)_2O(CH_2)_2OCH_3]$, triglyme and tetraglyme. Other suitable solvents include alkyl pyrrolidones such as N-methyl pyrrolidone and alkoxy ethyl ethers such as bis-[2-[2-methoxy-ethoxy]ethyl]ether. Diglyme is a particularly preferred solvent.

Additional components can be added to the solution of the invention, such as components which stabilize the solution over temperature variations or which improve the viscosity of the solution. A preferred additional component is acetic acid, which can increase the viscosity of the solution and also the solubility of the metal compounds, including $RhCl_3.4H_2O$.

The solutions of the present invention, which are noncorrosive, do not require additional chlorides such as lithium chloride or hydrochloric acid even when the solvent is a glycol derivative such as diglyme. This is in contrast to prior solutions such as those described in U.S. Pat. Nos. 4,475,483 and 4,382,017, which required such chlorides to prevent precipitation and destruction of the catalyst. The solutions of the invention are stable over a range of temperature of from about $-10°$ to $60°$ C. Additionally, the solutions are stable over time, with little or no breakdown or precipitation of the metal catalyst.

It has been found that the stability of solutions of the invention is independent of water content where the metal compounds are employed are $H_2PtCl_6.6H_2O$, $LiReO_4$ and $RhCl_3.4H_2O$. Where other rhenium compounds, such as $Re_2(CO)_{10}$, are substituted for $LiReO_4$, the water content of the solution may play a role in solution stability. For such solutions, it is preferred that the water content be maintained in a range of about 2 to 15 ml per 500 ml of solution, with about 7 ml $H_2O$ particularly preferred. Control of the water content in such a manner will prevent precipitation of metal compounds, such as the rhodium salt, where too little water is maintained in the system, or separation of compounds such as $Re_2(CO)_{10}$, where too much water is permitted to be present in the system.

Preferably, the solution contains three different metal compounds. It is believed that use of plural metal compounds in solution, and in particular use of three metal compounds in solution, gives the most beneficial results for reduction of automotive emissions, which requires balancing both oxidation and reduction conditions. In the most preferred embodiment, the solution contains $H_2PtCl_6.6H_2O$, $LiReO_4$ and $RhCl_3.4H_2O$. The preferred molar ratio of Pt:Re:Rh in this embodiment is about 1.5–2.5:1.0–2.0:0.5–1.5. For these preferred compound forms, the weight ratio of $H_2PtCl_6.6H_2O$:$LiReO_4$:$RhCl_3.4H_2O$ is about 3.0–4.0:0.4–1.4:0.5–1.5. The most preferred embodiment contains these compounds in a weight ratio of about 3.5:0.9:1.0, which corresponds to a molar ratio of about 1.0:1.44:1.92. The preferred weight concentration of these metal compounds in solution preferably is as follows:

| | |
|---|---|
| $H_2PtCl_6.6H_2O$ | 3.0–4.0 grams/liter |
| $LiReO_4$ | 0.4–1.4 grams/liter |
| $RhCl_3.4H_2O$ | 0.5–1.5 grams/liter |

The most preferred weight concentrations are 3.5 g/l of $H_2PtCl_6.6H_2O$, 0.88 g/l of $LiReO_4$, and 1.0 g/l of $RhCl_3.4H_2O$. For the preferred solution containing $H_2PtCl_6.6H_2O$, $LiReO_4$ and $RhCl_3.4H_2O$, it is preferred that the total metal compound content in the solution be about 5.4 grams per liter of solvent, with the relative proportions of each compound in the ratios given above.

The solutions of the present invention are useful in providing catalyst material for conversion of automotive emissions. In a preferred embodiment, the solution is maintained in a suitable container adjacent the incoming air intake to an automotive engine. As air passes into the engine, the metal compounds are injected or otherwise introduced into the air stream, and are carried into and through the engine. As the catalyst material is carried out of the combustion chamber into the exhaust portion of the system, where the catalyst is deposited in the exhaust system. The location of deposition in the exhaust system is controlled by factors such as the flow rate of the metal through the exhaust system, the temperature and pressure. The deposited catalyst then aids in conversion of CO, NOx and unburned hydrocarbons emitted from the engine. As the catalyst becomes spent, no physical replacement of the catalyst support system is necessary. Fresh catalyst is carried through the engine and deposited in the exhaust system.

The metal compounds are entrained from the solutions of the present invention into a gaseous phase, and eventually are vaporized, leaving the metal catalyst in the gaseous phase. The catalyst is carried to a point downstream of the combustion chamber, and precipitated or otherwise deposited onto a solid surface. Catalytic efficiency can be advantageously improved using solutions of the present invention.

Proper control of air flow rates, temperatures and pressures preferably will entrain and deposit the catalyst when the engine runs at relatively low idle speeds, which can be sufficient to deliver catalyst in quantities which will convert desired amounts of pollutants. Solutions of the present invention can be utilized to convert as much as 98% CO, 98% NOx, and 100% unburned hydrocarbons to $CO_2$, $N_2$, and $H_2O$. Two copending applications U.S. Ser. Nos. 840,860 and 841,357, each filed Feb. 25, 1992, contain further details and embodiments of suitable uses for solutions of the present invention, and the disclosure of those applications is incorporated herein by reference.

The following examples are illustrative of the invention.

EXAMPLE 1

One liter of diethylene glycol dimethyl ether (diglyme), grade pure, was stored for a day over 15 g of granulated KOH, pure for analysis, and then was distilled over potassium hydroxide under a reduced pressure (about 20 mm Hg).

150 ml of diglyme was poured onto a dispersion of 1,766 grams of $H_2PtCl_6.6H_2O$ in a 250 ml glass vessel. Then, the mixture was intensively mixed by a magnetic mixer to fully dissolve the residue, over a period of 1–2 minutes. The mixture was then intensively stirred for another 30 minutes.

A dispersion of 0,724 grams of $Re_2(CO)_{10}$ was added while mixing by a magnetic mixer to 150 ml of diglyme and heated to about 45° to 55° C. in a 250 ml glass vessel. After 30 to 40 minutes of mixing, the residue was fully dissolved and the solution was allowed to cool to room temperature.

2 ml of $H_2O$ and 5 ml of acetic acid were added to a dispersion of 0.499 grams $RhCl_3.4H_2O$, in a 50 ml glass vessel. The obtained mixture was mixed by magnetic mixer for one hour until fully dissolved. Then 20 ml of diglyme was added in drops while mixing. After 30 minutes of mixing, the solution was placed in a 250 ml glass vessel, and 3 ml of $H_2O$ and 5 ml of acetic acid were added to it while mixing. Mixing lasted for 5 minutes, and then 130 ml of diglyme were added. Mixing was continued for one more hour. The obtained solution became dark red in color.

The prepared diglyme solutions of $H_2PtCl_6.6H_2O$ and $Re_2(CO)_{10}$ were mixed in a 800 ml glass vessel for 15 minutes. The prepared solution of $RhCl_3.4H_2O$ was carefully added to this mixed solution, which was a yellow-orange color, while mixing; as a result, dimming of the resultant solution color from an opaque solution which refracted light to a solution which refracted less light was observed. Next, 2 ml of $H_2O$ were added to the solution, and the total volume of the solution was brought to 500 ml by addition of diglyme. The solution was thoroughly mixed for four hours. After 10 to 12 hours of settling of any excess undissolved metal compound, the solution was filtered through a glass filter of porosity 3. The obtained solution contained the following components: 0.6650 grams of Pt; 0.4410 grams of Re and 0.183 grams of Rh, which corresponds to the following molar ratios: 1.0:1.44:1.92.

The final solution was tested for temperature stability. The temperature of the solution was varied from −10° C. to 55° C., and the solution viscosity measured at various points over that range. FIG. 1 shows the viscosity obtained over the tested temperature range. It can be seen from FIG. 1 that the solution viscosity decreased as the temperature increased; however, the solution remained stable over the entire temperature range.

Long-term solution stability was also measured. The solution was maintained at a temperature of 80° C. for 20 hours without any noticeable change or breakdown. Tests at both room temperature and at −10° C. resulted in stability of the solution for over 40 days.

Figure 2:
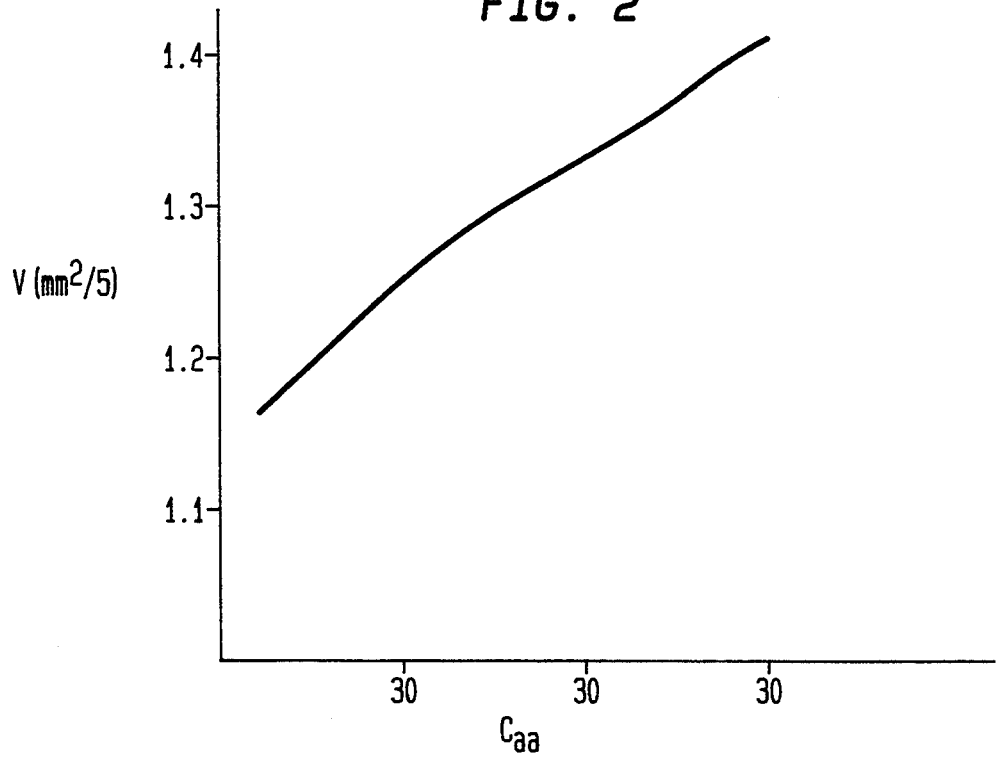
FIG. 2 is a graph of acetic acid concentration addition versus solution viscosity for solutions of the present invention.

The effect of acetic acid addition on solution viscosity was also measured. A series of solutions were prepared in accordance with this example having varied acetic acid volumetric concentrations. The resultant data are given in FIG. 2. FIG. 2 shows that an increase in acetic acid concentration yields increased solution viscosity.

EXAMPLE 2

One liter of a catalyst solution of the compounds $LiReO_4$, $H_2PtCl_6.6H_2O$ and $RhCl_3.4H_2O$ in diethylene glycol dimethyl ether was prepared as follows.

Diethylene glycol dimethyl ether (diglyme) was prepared as described in the previous example.

A diglyme solution of lithium perrhenate ($LiReO_4$) was prepared as follows. A dispersion of 10.65 grams of commercial ammonium compound $NH_4ReO_4$, grade "chem. pure", was dissolved in 100 ml of $H_2O$ at a temperature of 50° to 55 ° C. Next, 30 ml of an aqueous solution of lithium hydroxide containing 1.1 grams of LiOH was added to a warm solution of $NH_4ReO_4$. The solution was mixed by a magnetic mixer and heated to 50°–55 ° C., for three hours, and then the solution was evaporated to a volume of about 10 to 15 ml. Then, the concentrate was slightly diluted with about 20 to 25 ml water, and $CO_2$ was bubbled through the obtained solution until a pH of 6 to 7 was achieved. Next, the solution was filtered and evaporated until dry. The residue was further dried at a temperature of 55° to 65 ° C. in a vacuum ($10^{-2}$ mm Hg) for six hours. The obtained dry mixture, containing a specific lithium perrhenate and lithium carbonate admixture, was dissolved while mixing for one hour in 50 ml of diglyme and filtered. The sediment on the filter was washed in 15 ml of diglyme and the filtrates were mixed. The solution volume was brought to 100 ml by addition of diglyme and contained 0.739 grams of rhenium per 10 ml of solution. An aliquot of 11.9 ml was taken from 100 ml of the $LiReO_4$/diglyme solution for use as described below.

300 ml of distilled diglyme and 1 ml of $H_2O$ were added to 3.532 grams of $H_2PtCl_6.6H_2O$ in a 500 ml glass vessel and the mixture was intensively mixed by a magnetic mixer until complete dissolution occurred in 1 to 2 minutes. In so doing, a great number of bright orange-red drops were observed at the vessel bottom. After intensive mixing for 30 minutes, these drops were dissolved and a true solution of orange color was formed.

To dissolve $RhCl_3.4H_2O$, 20 ml of $H_2O$ was added to 0.998 grams $RhCl_3.4H_2O$ in a 150 ml glass vessel and the obtained mixture was mixed by magnetic mixer for one hour until complete dissolution occurred. Then, 100 ml of diglyme was added dropwise, while mixing, to the obtained solution. Mixing was continued for 30 minutes. The obtained solution assumed a dark red color.

The prepared diglyme solutions of $H_2PtCl_6.6H_2O$ and $LiReO_4$ were combined in a 1500 ml glass vessel and mixed for 15 minutes. The prepared solution of $RhCl_3.4H_2O$ was carefully added, while mixing, to this solution, and 20 ml of $H_2O$ were added as well. The total volume of the solution was brought by diglyme addition to 1000 ml, and the entire solution was thoroughly mixed for four hours. After 10 to 12 hours of storage, the solution was filtered through a glass filter with a porosity of 3. The obtained solution had a final volume of 1 liter. A 20 ml aliquot contained: 0.0266 grams of Pt, 0.0073 grams of Rh and 0.0176 grams of Re, which corresponds to a molar ratio of about 1.36:0.72:0.94.

EXAMPLE 3

0.0475 grams of $RhCl_3.4H_2O$ was mixed in 5 ml of N-methyl pyrrolidone at room temperature, with very weak solving observed. The mixture was heated to 80° C. for 5 minutes, dissolving the salt and forming a red-brown solution. The resulting solution was cooled and was stable.

0.0504 grams of $H_2PtCl_6.6H_2O$ was mixed in 5 ml of N-methyl pyrrolidone, dissolving the salt slowly. The mixture was heated to 80° C., quickly dissolving the remaining salt and forming a pale yellow solution. The resulting solution was cooled and was stable.

0.0222 grams of $LiReO_4$ was added to 0.3 ml diglyme. Dimethylpyrrolidone was added to bring the solution volume to 10 ml. The resulting solution was stable.

A solution was prepared by admixing 2 ml of the $RhCl_3.4H_2O$ solution, 4 ml of the $H_2PtCl_6.6H_2O$ solution, and 5 ml of the $LiReO_4$ solution. The combined solution was transparent red in color and contained 0.0190 grams of $RhCl_3.4H_2O$, 0.0403 grams of $H_2PtCl_6.6H_2O$, and 0.0153 grams of $LiReO_4$. The combined solution was stable.

EXAMPLE 4

0.0359 grams of $H_2PtCl_6.6H_2O$ was mixed with 5 ml of tetraglyme. While the salt did not initially dissolve, upon heating to 80° C. the salt fully dissolved, and the solution assumed a yellow-green color. The solution was stable.

0.0333 grams of $RhCl_3.4H_2O$ were dissolved in 0.2 ml $H_2O$, and 2.5 ml tetraglyme were then added to form a somewhat cloudy solution. Next, 0.3 ml $H_2O$ were added to the solution, and the solution volume was brought to 5 ml by addition of tetraglyme. The solution became transparent, and was stable.

An $LiReO_4$ sample containing 0.0222 grams of rhenium were concentrated in 0.3 ml of diglyme. Tetraglyme was added to form a solution having a total volume of 10 ml. The solution was stable.

A solution was prepared by admixing 4 ml of the $H_2PtCl_6.6H_2O$ solution, 3 ml of the $RhCl_3.4H_2O$ solution, and 5 ml of the $LiReO_4$ solution. A transparent red solution was formed containing 0.0200 grams of $H_2PtCl_6.6H_2O$, 0.0287 grams of $RhCl_3.4H_2O$, and 0.0153 grams of $LiReO_4$. The solution was stable.

What is claimed is:

1. A catalyst solution for converting combustion emissions comprising a compound of platinum, a compound of rhenium, a compound of rhodium, and a solvent selected from the group consisting of diglyme, triglyme, tetraglyme, an alkyl pyrrolidone, and an alkoxy ethyl ether, wherein no additional chloride-containing compounds are added to the solution.

2. A solution according to claim 1 wherein the Pt compound is $H_2PtCl_6.6H_2O$, the Re compound is $LiReO_4$ and the Rh compound is $RhCl_3.4H_2O$.

3. A solution according to claim 1 wherein the Pt compound is $H_2PtCl_6.6H_2O$, the Re compound is $Re_2(CO)_{10}$, and the Rh compound is $RhCl_3.4H_2O$.

4. A solution according to claim 1 further comprising acetic acid.

5. A solution according to claim 2 wherein the solvent is diglyme.

6. A catalyst solution consisting essentially of a compound of platinum, a compound of rhenium, a compound of rhodium, and a solvent selected from the group consisting of triglyme, tetraglyme, an alkyl pyrrolidone, and an alkoxy ethyl ether.

7. A solution according to claim 6 wherein the compounds are selected from the group consisting of $H_2PtCl_6.6H_2O$, $Re_2(CO)_{10}$, $Re_2O_7$, $LiReO_4$ and $RhCl_3.4H_2O$.

8. A solution according to claim 7 wherein the metal compounds are $H_2PtCl_6.6H_2O$, $LiReO_4$ and $RhCl_3.4H_2O$.

9. A solution according to claim 7 wherein the metal compounds are $H_2PtCl_6.6H_2O$, $Re_2(CO)_{10}$, and $RhCl_3.4H_2O$.

10. A solution according to claim 6 further comprising acetic acid.

11. A solution according to claim 8 wherein the solvent is diglyme.

12. A solution according to claim 9 wherein the weight ratio of $H_2PtCl_6.6H_2O:LiReO_4:RhCl_3.4H_2O$ is 3.0–4.0:0.4–1.4:0.5–1.5.

13. A solution according to claim 9 wherein the weight concentration of $H_2PtCl_6.6H_2O$ is 3.0–4.0 grams/liter, the weight concentration of $LiReO_4$ is 0.4–1.4 grams/liter, and the weight concentration of $RhCl_3.4H_2O$ is 0.5–1.5 grams/liter.

14. A catalyst solution comprising a compound of platinum, a compound of rhenium, a compound of rhodium, and a solvent selected from the group consisting of diglyme, triglyme, tetraglyme, an alkyl pyrrolidone, and an alkoxy ethyl ether.

15. A solution according to claim 14 wherein the platinum compound is $H_2PtCl_6.6H_2O$, the rhenium compound is selected from the group consisting of $Re_2(CO)_{10}$ and $LiReO_4$, and the rhodium compound is $RhCl_3.4H_2O$.

* * * * *